United States Patent
Shah

(10) Patent No.: US 8,703,212 B2
(45) Date of Patent: Apr. 22, 2014

(54) BASE MATERIAL FOR PHARMACEUTICAL AND/OR COSMETIC CREAM (HERBAL COMPOSITION FOR ITCHY OR INFECTED SKIN)

(75) Inventor: Eladevi Mahendra Shah, London (GB)

(73) Assignee: Viraj Shah, Varion Limited, London ( * ) Notice: Subject to any disclaimer, the term of this patent is extended or adjusted under 35 U.S.C. 154(b) by 1345 days.

(21) Appl. No.: 11/517,986

(22) Filed: Sep. 11, 2006

(65) Prior Publication Data

US 2007/0014749 A1    Jan. 18, 2007

(51) Int. Cl.
*A01N 65/00*     (2009.01)
*A61K 36/00*     (2006.01)

(52) U.S. Cl.
CPC ..................... *A61K 36/00* (2013.01)
USPC ........................................ 424/725

(58) Field of Classification Search
None
See application file for complete search history.

(56) References Cited

U.S. PATENT DOCUMENTS

| | | | | |
|---|---|---|---|---|
| 3,950,892 A | * | 4/1976 | Simkin | 47/1.01 R |
| 5,693,327 A | * | 12/1997 | Shah | 424/734 |
| 5,730,986 A | * | 3/1998 | Bandyopadhyay et al. | 424/761 |
| 5,939,085 A | * | 8/1999 | Jacobs et al. | 424/401 |
| 6,271,246 B1 | * | 8/2001 | Murad | 514/356 |
| 6,372,234 B1 | * | 4/2002 | Deckers et al. | 424/401 |
| 2002/0018788 A1 | * | 2/2002 | Jutila | 424/400 |
| 2005/0069598 A1 | * | 3/2005 | Ribnicky et al. | 424/740 |

FOREIGN PATENT DOCUMENTS

| JP | 06-025663 | * | 2/1994 |
|---|---|---|---|
| JP | 10-226787 | * | 8/1998 |

OTHER PUBLICATIONS

Yousif et al "Headspace Volatiles and Physical Characteristics of Vacuum-microwave, Air and Freeze-dried Oregano (*Lippia berlandieri* Schauer" Journal of Food Sciend, vol. 65, No. 6, 2000.*

* cited by examiner

*Primary Examiner* — Bethany Barham

(57) ABSTRACT

This is the process for preparation of a novel base material for manufacturing cream, comprising of cooling and soothing agent on the skin Ghee 12%, Coconut oil (*Cocos nucifera*) 12%, Water 65%, and mixture of Cetyl alcohol, Laxemul (Glyceryl stearate+PEG 100 stearate) and vegetable Glycerol in ratio of 4:5:1 respectively totaling 10%. Freeze dried water extracts of herbs, *Cassia tora* 0.005%, *Centratherum anthelminticum* 0.005% and *Melia azadirachta* 0.005%, Neem kernel oil 0.48%, Rose oil 0.02%. To investigate the effect of herbal compositions suspended in a cream based on novel vehicle Ghee (clarified butter) and develop natural cream useful for treatment of any sort of itchy and or infected skin, impetigo, children eczema, psoriasis, acne, and athlete's foot. The base of the cream is useful to those individuals who react to conventional creams containing chemicals. Theme chemicals are proven skin sensitizers such as Chlorocresol, cetosteryl alcohol, Parabens etc.

14 Claims, No Drawings

BASE MATERIAL FOR PHARMACEUTICAL AND/OR COSMETIC CREAM (HERBAL COMPOSITION FOR ITCHY OR INFECTED SKIN)

BACK GROUND OF INVENTION

Purpose: To investigate the effect of herbal compositions suspended in a cream based on novel vehicle "Ghee" (clarified butter) and develop natural cream useful for treatment of children eczema, psoriasis, acne, and athlete's foot. This invention relates to the manufacture and use of herbal compositions in the cream form for the treatment of itchy or infected skin such as in impetigo, acne (on face, forehead scalp and on the back of the body) and fungal infection of skin and nails.

Vegetable origin emulsifiers and stabilisers are used. Here is feasibility of preparing a cream and also by using only natural ingredients as a preservative. The base of the cream is intended for those people who have reaction to many skin sensitizers which are used in conventional creams. This is for topical application only. The use of Ghee and coconut oil in the formulation of cosmetic composition has a favourable effect on skin (soothing and cooling sensation). The cream as such it is meant as non hydrocortisone no lanolin no fragrance cream. The high concentration of Ghee in original formula was found to be effective but smell of ghee was not tolerable by some of the customers. Now that problem is overcome and this formulation found very useful for making natural cream. Herbs and Ghee are working as protective element for cream as well as curative element in function on the skin.

Acne

Acne is a disease of the pilosebaceous unit. It predominantly affects the face, back and chest. Peri-oral area of the face is more vulnerable. Still acne is not a simple face skin disorder, few patients with severe acne on the back or chest who have non-on the face.

Acne is a mixture of, inflammation-infection process and favoured by the presence of time oriented hormonal imbalance.

Most commonly found anaerobes and/or aerobe-bacteria in the acne are *Staphylococcus albus, Staphylococcus epidermidis, Pitirosporum ovale, Propioniibacterium acnes*.

One gentleman was suffering from acne on his face and also on his back for many years. He was reluctant for antibiotics because he knew that antibiotics gave him more trouble. He came to me for natural treatment for keloids he was suffering for long time. I gave him oral compound and herbal cream to apply one month supply, on 25th day of treatment he came to me for cream supply. At that time I counted spots on his back out of 33 spots 25 spots were healed. I realised that this is Propionibacterium acnes has disappeared.

Acne and Immune Response:

As previously stated acne is a mixture of, inflammation-infection process and favoured by the presence of time oriented hormonal imbalance.

Pustules resolve faster than papules. In pustules natural healing process is faster because of polymorphonucleocyte activity and in papules the natural healing process is slower because here it depends on lymphocyte activity. Here this lymphocyte activity remains helpful in further growth of the comedones. Macules are the end result of inflamed lesions, most persist for 7 days and they can linger for several weeks. Present invention is useful for prevention of further scarring.

Facial Scarring

It is well recognised that facial scarring and scars on the back are associated with long standing changing guards-games played by different sorts of bacteria fungi and immune response of the body in the form of production and presentation of lymphocyte and polymorphonucleocytes.

Fungal Nail Infection and Immune Response

The skin in some people react to external and internal changes very fast such as drinking alcohol, washing with alkaline soap, increased sweating in summer and more humid skin environment. All these skin sensitising factors could bring circulatory changes on the skin and inside the nail beds.

It is well recognised that alkalinity on the skin initiates or promotes fungal infections. In long journey of antibiotics, resistance development and hide and seek games played by organisms the present invention remains most blissful.

Method of Making the Cream

Oil Phase:

In a sterile vessel first take "Ghee" 12 Kg and add coconut oil 12 kg, Cetyl alcohol 4 Kg, Laxemul Glyceryl stearate+ PEG 100 stearate) 5 kg, vegetable Glycerine 1 Kg and Neem kernel oil 0.500 kg. Heat all of the above ingredients up to 98° C. melt it completely until it becomes homogenous oil phase mixture. Let it cool down up to temperature 75° C. And then it will be ready for mixing with water phase.

Water Phase:

65 liters of deionised water (sterile water) heat it up to 100° C. and let it cool down up to temperature 75° C. Then it will be ready mixing with oil phase.

Mix oil Phase and water by high shear mixing with automatic stirrer for 2-3 minutes continuously stirring until it reaches 30° C. Now add 5 milligrams of freeze dried water extracts of herbs Cassia tora, Centratherum anthelminticum and Melia azadirachta 0.005% each dissolved in 485 milliliters of deionised water and add 20 ml of rose oil and mix well. Then take out the cream in to a separate vessel and allow it to settle down. Ph will be in range of 5.5 to 6.5.

Example 1 and Example 2 are from the priority date U.S. patent application Ser. No. 10/129,794.

Example 3, Example 4 and Example 5 are in the present application CONTINUATION-IN-PART.

EXAMPLE 1

A preferred embodiment of the present invention is a cream made up as follows:

Ghee 3 kg

Water boiled and cooled freezing temperature 3 liters

Freeze dried extract of Centratherum anthelminticum 5 g (2 kilogram raw material of the seeds provided 100 grams of freeze dried powder)

Medicated Sesame oil 500 ml (500 ml sesame oil treated with *Centratherum anthelminticum* seeds 100 gm, Rose petals 100 gm, *Melia azadirachta* leaves 100 gm, *Cassia tora* seeds 50 gm and some water to make a paste}.

To make up the cream, the ghee is first hydrolysed in a clean stainless steel vessel with three liters of water (boiled and cooled freezing temperature) then add 500 ml of medicated oil.

EXAMPLE 2

A preferred embodiment of the present invention is a cream made up as follows:

Ghee 3 kg
Water boiled and cooled freezing temperature 3 liters
Freeze dried extract of *Centratherum anthelminticum* 5 gms (2 kilogram raw material of the seeds provided 100 grams of freeze dried powder)
Medicated Sesame oil 500 ml
(*azadirachta* leaves 100 gm, and some water to make a paste).

To make up the cream, the ghee is first hydrolysed in a clean stainless steel vessel with three liters of water (boiled and cooled freezing temperature) then add 500 ml of medicated oil. (500 ml sesame oil treated with *Centratherum anthelminticum* seeds 100 gm, Rose petals 100 gm, *Melia azadirachta* leaves 100 gm, and some water to make a paste).

Laboratory Results:

Test for Total Viable Count

The above sample was tested for total viable count by pour plate. Aerobic, anaerobic and fungal methods were employed. A dilution rate of 1 in 10 was used.

Results

| Aerobic Tryptone Soya Agar @ 35° C. for 7 days | Anaerobic Tryptone Soya Agar @ 35° C. for 7 days | Saboraud Dextrose for 7 Agar @ 35° C. for 7 days |
|---|---|---|
| 0, 0 | 0, 0 | 0, 0 |

Comments

As the test employed a dilution rate of 1:10 the theoretical sensitivity of the test, using duplicate plates is 5 colony-forming units per ml.

The sample passes the BP guidance for preparations for topical use (A316).

Additional testing that Should be considered for the future would be the absence of *Pseudomonas aurigenosa* and *Staphylococcus aureus*.

Due to absence of bacteria in this sample it is safe to assume that both the above have been satisfied.

The cream was made in June 2002; the Batch No. AFCJI, Report date 5 Jul. 2002, tested by Craig Hughes BSc. Microbiologist at Pharmaceutical Quality Assurance Services
Edgware Community Hospital
Edgware Middlesex HA8 0AD

EXAMPLE 3

HAND CREAM and Infantile-Eczema

For Skin Preparation-Moisturizer % Weight for Weight (i) Composition

| Ingredients | Inci Name | Amount | Purpose |
|---|---|---|---|
| Water | Aqua | 64.90% | |
| Ghee | "Ghee" | 12% | Base, preservative |
| Coconut oil | *Cocos nucifera* | 12% | Excipient |
| Cetyl alcohol | Cetyl alcohol | 4% | Emulsifier |
| Laxemul | Glyceryl stearate +PEG 100 stearate | 5% | Stabilizer |
| Glycerine | Glycerol | 1% | Binding Agent |
| Vitamin E | Tocoferol | 0.1% | Binding agent |
| Jasmine, Rose, Neem and Black cumin oil | | 0.5% | Herbs Herb |
| Grape Fruit seeds extract | | 0.5% | |

This product treats eczema in children (age above 6 months), psoriasis, lichen planus and all sorts of itchy skin disorders.

product treats skin disorders such as infantile eczema, achrodermatitis, very dry flaky, itchy seborrhoeic dermatitis.

Laboratory Results:

BP Challenge Test-5 Organisms for Total Viable Count

Method: MM002b Units: cfu/g or ml Batch: 04Y0486
Date received 29 May 2003 Testing finished 14 Jul. 2003

| Organisms tested: | Recovery cfu g or ml 28 days: |
|---|---|
| *Pseudomonas aeruginosa* ATCC 9027 | <10 |
| *Staphylococcus aureus* NCTC 10788 | <10 |
| *Escherichia coli* NCTC 8545 | <10 |
| *Aspergillus niger* IMI 149007 | <10 |
| *Candida albicans* NCTC NCPF 3179 | <10 |

Recovery cfu g or ml was monitored at interval of 2 days, 7 days, 14 days and 28 days.

Results:
Initial microbial status: Bacteria<10 cfu/g;
Yeast/moulds<10 cfu/g.

At the completion of testing, this sample fulfils the requirements of the BP (1999) for the adequate preservation of topical products.

Comments:
BP(1999) criteria
Bacteria: 2 log and 3 log reduction after 48 hours and 7 days respectively, with no increase thereafter.

The Test was performed by Microbiologist John Reed at Donnington Laboratories Limited. Unit 3, Donnington Park, Birtham Road, Chichester, West Sussex PO20 7DU

EXAMPLE 4

Eczema, Psoriasis, Lichen Planus

For Skin Preparation-Moisturizer % Weight for Weight (i) Composition

| Ingredients | Inci Name | Amount | Purpose |
|---|---|---|---|
| Water | Aqua | 65% | |
| Ghee | "Ghee" | 12% | Base, preservative |

-continued

| (i) Composition | | | |
|---|---|---|---|
| Ingredients | Inci Name | Amount | Purpose |
| Coconut oil | Cocos nucifera | 12% | Excipient |
| Cetyl alcohol | Cetyl alcohol | 4% | Emulsifier |
| Laxemul | Glyceryl stearate +PEG 100 stearate | 5% | Stabilizer |
| Glycerine | Glycerol | 1% | Binding Agent |
| Vitamin E | Tocoferol | 0.1% | masking smell |
| Black cumin seed Freeze dried extract | | | |
| Centratherum anthelminticum | | 0.005% | Herb |
| "Neem" | Melia azadirachta | | |
| (Freeze dried whole plant extract) | | 0.005% | Herb |
| De-ionised water | | 0.37% | |
| Neem kernel oil | | 0.5% | |
| Melia azadirachta | | | |
| Grape fruit seeds Extract | | | |
| Citrus grandis | | 0.5% | |
| Vitamin E | Tocopherol | 0.1% | |
| Rose oil | Rosa Edward | 0.02% | Good smell |

Laboratory Results:

BP Challenge Test-5 Organisms for Total Viable Count

Method: MM002b Units: cfu/g or ml

Batch: 04V0485/PC Manufactured 23 Apr. 2003

Date received 29 May 2003 Testing finished 14 Jul. 2003

| Organisms tested: | Recovery cfu g or ml 28 days: |
|---|---|
| Pseudomonas aeruginosa ATCC 9027 | <10 |
| Staphylococcus aureus NCTC 10788 | <10 |
| Escherichia coli NCTC 8545 | <10 |
| Aspergillus niger IMI 149007 | 70 |
| Candida albicans NCTC NCPF 3179 | <10 |
| Recovery cfu g or ml was monitored at interval of 2 days, 7 days, 14 days and 28 days. | |

Results:

Initial microbial status: Bacteria<10 cfu/g;

Yeast/moulds<10 cfu/g.

At the completion of testing, this sample fulfils the requirements of the BP (1999) for the adequate preservation of topical products.

Comments:

BP (1999) criteria

Bacteria: 2 log and 3 log reduction after 48 hours and 7 days respectively, with no increase thereafter;

Yeasts/moulds: 2 log reduction within 14 days, with no increase thereafter.

The Test was performed by Microbiologist John Reed at Donnington Laboratories Limited.

Unit 3, Donnington Park, Birtham Road, Chichester, WEST SUSSEX PO20 7DU UK

EXAMPLE 5

Impetigo, Acne, Athlete's Foot

For Skin Preparation-Moisturizer % Weight for Weight

| (i) Composition | | | |
|---|---|---|---|
| Ingredients | Inci Name | Amount | Purpose |
| Water | Aqua | 65% | |
| Ghee | "Ghee" | 12% | Base, preservative |
| Coconut oil | Cocos nucifera | 12% | Excipient |
| Cetyl alcohol | Cetyl alcohol | 4% | Emulsifier |
| Laxemul | Glyceryl stearate +PEG 100 stearate | 5% | Stabilizer |
| Glycerine | Glycerol | 1% | Binding Agent |
| Vitamin E | Tocoferol | 0.1% | Binding agent |
| Grape Fruit seeds Extract | | | |
| | Citrus grandis | 0.5% | |
| Cassia tora seeds | | | |
| Freeze dried extract | | 0.005 | Herb |
| Black cumin seed | | | |
| Freeze dried extract | | | |
| Centratherum anthelminticum | | 0.005% | Herb |
| "Neem" | Melia azadirachta | | |
| (Freeze dried whole plant extract) | | 0.005% | Herb |
| De-ionised water | | 0.365% | |
| Neem kernel oil | | 0.5 % | |
| Rose oil | Rosa Edward | 0.02% | Good smell |

By using Freeze dried extract of Cassia tora, Centratherum anthelminticum and Freeze dried extract of Melia azadirachta where in claim 6 effectiveness of the product is seen clinically.

Laboratory Results:

BP Challenge Test-5 Organisms for Total Viable Count

Method: MM002b Units: cfu/g or ml Batch: 040499/FC Manufactured 23 Apr. 2003

Date received 29 May 2003 Testing finished 14 Jul. 2003

| Organisms tested: | Recovery cfu g or ml 28 days: |
|---|---|
| Pseudomonas aeruginosa ATCC 9027 | <10 |
| Staphylococcus aureus NCTC 10788 | <10 |
| Escherichia coli NCTC 8545 | <10 |
| Aspergillus niger IMI 149007 | 90 |
| Candida albicans NCTC NCPF 3179 | <10 |
| Recovery cfu g or ml was monitored at interval of 2 days, 7 days, 14 days and 28 days. | |

Results:

Initial microbial status: Bacteria<10 cfu/g;

Yeast/moulds<10 cfu/g.

At the completion of testing, this sample fulfils the requirements of the BP (1999) for the adequate preservation of topical products.

Comments:

BP (1999) criteria

Bacteria: 2 log and 3 log reduction after 48 hours and 7 days respectively, with no increase thereafter.

Yeasts/moulds: 2 log reduction within 14 days, with no increase thereafter.

The Test was performed by Microbiologist John Reed at Donnington Laboratories Limited Unit 3, Donnington Park, Birtham Road, Chichester, WEST SUSSEX PO20 7DU UK.
Laboratory Results Comparison of the Bactericidal Properties of Anjali Face Cream Against Propionibacterium Acnes and Staphylococcus Epidermidis Objective To evaluate in vitro the bactericidal activity of the Anjali Face cream in the respect of the two organisms most commonly reported as being implicated in acne vulgaris and to compare this with an appropriate benchmark product with claimed efficacy against spots and acne.
Test Products Anjali Face Cream: Pharma Herbeli, batch BN 0470498/FC, manufactured 23 Mar. 2003

Benchmark: Oxy 10 Lotion: Glaxo Smithcline, batch 213A, expiry date December 2005, was containing 10% w/w benzyl peroxide.
Results Under experimental conditions employed, Anjali Face Cream reduced both the *Propionibacterium acnes* and *Staphylococcus epidermidis* innocula by >99% within 10 minutes.
Comments/Conclusions Under in vitro conditions, Anjali Face Cream demonstrates bactericidal activity against *Propionibacterium acnes* NCTC 737 and *Staphylococcus epidermidis* ATCC 12228 representing the two micro-organisms most commonly reported as implicated in acne vulgaris. Activity against these organisms was comparable to a benzyl peroxide based benchmark product, marketed as "maximum strength treatment for stubborn spots and acne".

The Test was performed by Microbiologist John Reed at Donnington Laboratories Limited Unit 3, Donnington Park, Birtham Road, Chichester, WEST SUSSEX PO20 7DU UK by using Freeze dried extract of *Cassia tora*, *Centratherum anthelminticum* and Freeze dried extract of *Melia azadirachta* where in claim 6 effectiveness of the product is compared with BENCHMARK OXY10 LOTION GLAXO SMITHKLINE, BATCH 213A CONTAINING 10% W/W BENZYL PEROXIDE.

EXAMPLE 6

For Skin Preparation-Moisturizer % Weight for Weight

| (i) Composition | | |
|---|---|---|
| Ingredients | Inci Name | Amount |
| Water | Aqua | 51.388% |
| Ghee | "Ghee" | 18% |
| Coconut oil | *Cocos nucifera* | 20% |
| Cetyl alcohol | Cetyl alcohol | 4% |
| Laxemul | Glyceryl stearate +PEG 100 stearate | 5% |
| Glycerine | Glycerol | 0.2% |
| Vitamin E | Tocoferol | 0.1% |
| Grape Fruit seed extract | *Citrus grandis* | 0.5% |
| Black cumin seed extract | | |
| | *Centratherum anthelminticum* | 0.012% |
| "Neem" kernel oil Mixed oil | *Melia azadirachta* | 0.1 % |
| Neem | *Melia azadirachta* | |
| Rose | Rosa Edward | 0.7% |
| Seeds of black cumin | | |

EXAMPLE 7

For Skin Preparation-Moisturizer % Weight for Weight

| (i) Composition | | |
|---|---|---|
| Ingredients | Inci Name | Amount |
| Water | Aqua | 63.388% |
| Ghee | "Ghee" | 6% |
| Coconut oil | *Cocos nucifera* | 20% |
| Cetyl alcohol | Cetyl alcohol | 4% |
| Laxemul | Glyceryl stearate +PEG 100 stearate | 5% |
| Glycerine | Glycerol | 0.2% |
| Vitamin E | Tocoferol | 0.1% |
| Grape Fruit seed extract | *Citrus grandis* | 0.5% |
| Black cumin seed extract | | |
| | *Centratherum anthelminticum* | 0.012% |
| "Neem" kernel oil Mixed oil | *Melia azadirachta* | 0.1 % |
| Neem | *Melia azadirachta* | |
| Rose | Rosa Edward | 0.7% |
| Seedsof black cumin | | |

Example 1 to Example 6 are successful.

Example 7 was a failure in concern of stability. Laboratory results: Antimicrobial preservative efficacy test was performed on the specified cream in Example 7 by Pharmaceutical Quality Assurance Services. Results: Log Reduction showed as follows: Fungi *Candida albicans* 0.07 at 48 hours, −0.50 at 7 days of interval, 0.13 at 14 days of interval, −0.25 at 28 days of interval. Conclusion: The amount of Ghee as specified in Example 3 to Example 6 is perfect. The % of the minimum amount of Ghee would be 12%, below that level there would be failure of self protective mechanism of the cream against the fungus.

I tried to reduce the amount of Ghee in the above batch of cream from 18% to 6% but by inclusion of less amount of Ghee in the cream, it did not work perfectly. It could not protect the cream from growth of fungus in the cream.

SUMMARY OF THE INVENTION

1. A method of making the cosmetic and/or Pharmaceutical cream comprising the following steps:

a) First preparing an oil phase by adding Ghee, coconut oil, Cetyl alcohol, Laxemul, vegetable glycerine, and Neem kernel oil and sesame oil to a sterile vessel, heating said vessel to temperature of 98° C. and next cooling said vessel to a temperature 75° C.;

b) Second, preparing a water phase by heating 65 liters of deionised water to 100° C. and next cooling said deionised water to a temperature 75° C.;

c) Third, mixing said water phase with said oil phase;

d) Forth, adding freeze dried water extracts of *Cassia tora, Melia azadirachta,* and *Centratherum anthelminticum* 5 mg, and dissolving said extracts to 485 milliliters of deionised water and adding 20 ml of rose oil to said freeze dried extracts.

According to a first aspect of the present invention, there is provided a base material for medicated cream and also for cosmetic creams. The base material with herbal Composition for use in the treatment of skin disorders itchy or infected skin such as impetigo, acne (on face, forehead scalp and on the back of the body) and fungal infection of skin and nails, which composition comprises extracts derived from the seeds of the plant *Centratherum anthelminthicum*. Example 1 The product treats skin disorders such as infantile eczema, achrodermatitis, very dry flaky, itchy seborrhoeic dermatitis.

According to second aspect of the present invention, there is provided a base material for medicated cream and also for cosmetic creams. The base material with herbal Composition for use in the treatment of skin disorders itchy or infected skin such as children eczema, achrodermatitis (those ladies on HRT treatment or on beta blockers are more vulnerable). Example 3

According to third aspect of the present invention, there is provided a base material for medicated cream and also for cosmetic creams. The base material with herbal Composition for use in the treatment of skin disorders such as acne and/or fungal infection and/or fungal infections of the nails, which composition comprises extracts derived from the seeds of the plant *Centratherum anthelminthicum* fruit-oil and extract from leaves, bark, roots of the plant *Melia azadirachta* and extracts derived from the seeds of the plant *Cassia tora*. Example 5

The product treats skin disorders such as acne vulgaris and spots, infection due to *Propionibacterium acnes* and/or fungal infection and/or fungal infections of the nails and impetigo.

According to fourth aspect of the present invention, there is provided a base material for medicated cream and also for cosmetic creams. The base material with herbal Composition for use in the treatment of skin disorders such as psoriasis, eczema, lichen planus, lichen sclerosus and lichen simplex. To develop natural cream useful for treatment of children eczema and psoriasis in children. Example 4

The product treats eczema in children (age above 6 months), psoriasis, lichen planus and all sorts of itchy skin disorders.

According to fifth aspect of the present invention, there is provided a base material for medicated cream and also for cosmetic creams. The base material with herbal Composition for use in the treatment of skin disorders such as itchy skin or infected skin through the administration of extracts derived from at least one member of the group consisting of the plants *Centratherum anthelminticum, Melia azadirachta, Cassia tora*. Example 2

The product treats skin disorders such as acne vulgaris and spots, infection due to *Propionibacterium acnes* and/or fungal infection and/or fungal infections of the nails and impetigo.

The base material for medicated cream and also for cosmetic creams of the present invention may be dispersed in a suitable carrier for topical application as a cream, gel, ointment or lotion, or may be in the form of a soap, shampoo. Alternatively, the composition may be formulated in a tablet form, or composition may be formulated and made spray dried extract.

Preferably, the composition spray dried extract is dispersed in a carrier suitable for topical application comprising ghee, which is clarified butter.

The compositions of the present invention help to break the cycles of pruritus-inflammation-pruritus, and of infection-inflammation-pruritus, thereby promoting faster healing of acute, sub-acute and chronic bacterial and fungal infection of the skin and fungal of nails. The compositions of the present invention are additionally useful in reducing the effects of stress and reinforcing immune response.

Extracts from *Centratherum anthelminticum, Melia azadirachta* disperse in a sesame oil and cream was formulated with ghee and antimicrobial preservative efficacy test was performed using *Propionibacterium acnes* NCTC 737 was introduced in a cream Inoculum count cfu/ml $2.1 \times 10^5$ and significant results were seen logarithm reduction unto 5.32 was achieved at the 7 days inoculation test and 14 days inoculation tests.

Extract from *Cassia tora* dispersed well with yogurt and heated and then applied on impetigo worked well. The activity was dose dependent.

Results and Conclusion:
1. Ghee and Coconut oil blended together nicely also Cetyl alcohol and Laxemul, when heated together all mixing well.
2. Phase one, phase two and mixing of herbal extract was done nicely. Stability of cream is achieved perfectly.
3. Life of the cream is very long lasting as effectiveness of herbs also maintained for longer period than other conventional creams.
4. Personal skincare base material useful in cosmetic and pharmaceutical industry containing Natural preservative, natural harmless vehicle and providing treatments for many skin conditions.
5. Free from steroids, free from lanolin and totally free from all potential skin sensitizers.

Shah E. M. 2003 Jul. 15; 2006 Aug. 16 Copyright

The invention claimed is:

1. A method of making a cosmetic and/or Pharmaceutical cream comprising at least 12% by weight of ghee and also coconut oil, Cetyl alcohol, (glyceryl stearate+PEG100 stearate), vegetable glycerine, neem kernel oil (*Melia azadirachta*), rose oil, grape fruit seed extract (*Citrus grandis*), 0.005% by weight of freeze dried *Cassia tora* seeds extract, 0.005% by weight of freeze dried black cumin seed extract (*Centratherum anthelminticum*), Vitamin E, 0.005% by weight of freeze dried neem leaf extract (*Melia azadirachta*), and optionally jasmine oil (*Jasminum grandiflorum*) comprising: (a) preparing an oil phase in a sterile stainless steel vessel by adding Ghee, coconut oil, Cetyl alcohol, (glyceryl stearate+PEG100 stearate), vegetable glycerine, and Neem kernel oil heating to temperature of 98° C. to from a homogenous oil phase mixture and allowing the mixture to cool to temperature 75° C.; (b) preparing a water phase by heating 65 liters of deionised water to 100° C. and allowing it to cool to temperature 75° C.; (c) mixing the oil and water phases together using high shear mixing with an automatic stirrer for 2-3 minutes and then stirring continuously until the temperature of the mixture reaches 30° C.; (d) adding vitamin E, grape fruit seed extract, freeze dried extracts of Melia azadirachta, *Centratherum anthelminticum* and *Cassia tora* seed dissolved in 485 ml deionised water; (e) adding 20 ml of rose oil and optionally jasmine oil; followed by stirring and adjustment of pH of the resulting mixture to between 5.5 to 6.5.

2. A Cosmetic and/or pharmaceutical cream prepared using the method defined in claim 1.

3. A method of making a cream according to claim 1, 12-50 wt % Ghee, 12 wt % coconut oil, 4 wt % Cetyl alcohol, 5 wt % (glyceryl stearate+PEG100 stearate), 1 wt % glycerol and 0.5 wt % Neem kernel oil.

4. A method of making a cream according to claim 1, comprising 12 wt % ghee, 12 wt % coconut oil, 4 wt % cetyl alcohol, 5 wt % (glyceryl stearate+PEG100 stearate), 1 wt % glycerol and 0.5 wt % neem kernel oil.

5. The method of claim 1 wherein mixing of the oil and water phases is carried out at 75° C.

6. The method of claim 1 wherein the pH of the final cream is in the range of 5.5 to 6.5.

7. The method of claim 1 wherein 0.005 wt % *Cassia tora* seed freeze dried extract, 0.005 wt % black cumin seed freeze dried extract, and 0.005 wt % neem leaf freeze dried extract are included in the cream by dissolving in 0.37-0.365 wt % deionised water that further includes 0.02 wt % rose oil.

8. A cream for use in the treatment of itchy or infected skin disorders comprising about 12% by weight of ghee, coconut oil, Cetyl alcohol, Glyceryl stearate+PEG100 stearate, vegetable glycerine, neem kernel oil (*Melia azadirachta*), rose oil, grape fruit seed extract (*Citrus grandis*), 0.005% by weight of freeze dried seed extract of *Cassia tora*, 0.005 by weight freeze dried extract of *Melia azadirachta* leaf, 0.005% by weight of freeze dried seed extract of black cumin (*Centratherum anthelminticum*), vitamin E, [and 0.005% by weight of freeze dried seed extract freeze of *Cassia tora* along, with neem leaf (*Melia azadirachta*) plus 0.005% by weight of freeze dried seed extract of the black cumin (*Centratherum anthelminticum*), wherein the freeze dried seed extract of cassia tora, the freeze dried seed extract of black cumin (*Centratherum anthelminticum*), and the neem leaf freeze dried extract (*Melia azadirachta*) are dissolved in about 0.365-0.37% by weight of deionised water and about 0.02% by weight of the rose oil.

9. The cream of claim 8, wherein the itchy or infected skin disorder is dry flaky, itchy seborrhoeic dermatitis, achrodermatits, eczema, athlete's foot, psoriasis, lichen planus, lichen simplex, lichen sclerosus, impetigo, acne vulgaris, or infection caused by Propioni bacterium acnes.

10. A cream for use in the treatment of fungal infections of the skin and nails comprising at least 12% by weight of ghee, coconut oil, Cetyl alcohol, (Glyceryl stearate+PEG100 stearate), vegetable glycerine, neem kernel oil (*Melia azadirachta*), rose oil, grape fruit seed extract (*Citrus grandis*), 0.005% by weight of cassia tora freeze dried seeds extract, 0.005% by weight of freeze dried seed extract of black cumin (*Centratherum anthelminticum*), vitamin E, and 0.005% by weight of neem freeze dried leaf extract (*Melia azadirachta*).

11. The cream of claim 8 wherein the skin disorder is eczema in children older than six months.

12. The cream of claim 8 wherein the cream further comprises jasmine oil (*Jasminum grandiflorum*).

13. The cream of claim 8 wherein the cream comprises 12-50 wt % ghee, 12 wt % coconut oil, 4 wt % cetyl alcohol, 5 wt % (Glyceryl stearate+PEG 100 stearate), 1 wt % glycerol, 0.5 wt % neem kernel oil.

14. The cream of claim 8 wherein the cream has a pH between 5.5 and 6.5.

* * * * *